US011935009B2

(12) United States Patent
Chen et al.

(10) Patent No.: US 11,935,009 B2
(45) Date of Patent: Mar. 19, 2024

(54) INTEGRATING HEALTHCARE SCREENING WITH OTHER IDENTITY-BASED FUNCTIONS

(71) Applicant: Turing Video, San Mateo, CA (US)

(72) Inventors: Weiwei Chen, Belmont, CA (US); Chien-Yu Chen, San Mateo, CA (US); Zhengyang Ma, San Mateo, CA (US); Chethan Kothwal, San Mateo, CA (US)

(73) Assignee: TURING VIDEO, San Mateo, CA (US)

( * ) Notice: Subject to any disclaimer, the term of this patent is extended or adjusted under 35 U.S.C. 154(b) by 316 days.

(21) Appl. No.: 17/225,935

(22) Filed: Apr. 8, 2021

(65) Prior Publication Data

US 2022/0328142 A1 Oct. 13, 2022

(51) Int. Cl.
*G06Q 10/10* (2023.01)
*G06K 7/14* (2006.01)
(Continued)

(52) U.S. Cl.
CPC ......... *G06Q 10/105* (2013.01); *G06K 7/1417* (2013.01); *G06K 7/1447* (2013.01);
(Continued)

(58) Field of Classification Search
CPC ............. G06Q 10/105; G06Q 10/1091; G06Q 50/265; G06K 7/1417; G06K 7/1447;
(Continued)

(56) References Cited

U.S. PATENT DOCUMENTS 11,051,701 B1 * 7/2021 Gaines ...................... G06T 7/73
11,170,894 B1 * 11/2021 Kocher ................ A61B 5/1176
(Continued)

OTHER PUBLICATIONS

Maras, E. (2020). DigitalSignageToday.com—networld media group: Digital signage, kiosks take COVID-19 head on. Weblog post. Newstex Trade & Industry Blogs, Newstex. Jul. 14, 2020. (Year: 2020).*

(Continued)

*Primary Examiner* — Jonathan P Ouellette (57) ABSTRACT

The present invention extends to methods, systems, and computer program products for integrating healthcare screening with other identity-based functions. In general, components facilitating healthcare screening interoperate with and/or are integrated into other systems, including facility access, identity, time keeping, payroll, etc. Aspects of the invention include using facial recognition to improve healthcare screening and satisfy governmental regulations. A thermal scanner can include a camera and an InfraRed (IR) camera. The thermal scanner can collect a facial image and derive a temperature for a person (e.g., from an IR image). The thermal scanner can also collect or access previously collected healthcare screening questionnaire answers. The collected temperate and healthcare screening questionnaire answers can be used to control access to the facility. For example, the person can be denied access when the collected temperature exceeds a defined temperate threshold and/or healthcare screening questionnaire answers indicate the person may be sick.

14 Claims, 7 Drawing Sheets

(51) Int. Cl.
| | |
|---|---|
| *G06K 19/06* | (2006.01) |
| *G06Q 10/06* | (2023.01) |
| *G06Q 10/105* | (2023.01) |
| *G06Q 10/1091* | (2023.01) |
| *G06Q 30/02* | (2023.01) |
| *G06Q 30/06* | (2023.01) |
| *G06Q 40/08* | (2012.01) |
| *G06Q 50/26* | (2012.01) |
| *G06V 40/16* | (2022.01) |
| *G07C 9/25* | (2020.01) |
| *G16H 10/20* | (2018.01) |
| *G16H 50/30* | (2018.01) |

(52) U.S. Cl.
CPC ... *G06K 19/06037* (2013.01); *G06Q 10/1091* (2013.01); *G06Q 50/265* (2013.01); *G06V 40/166* (2022.01); *G06V 40/172* (2022.01); *G07C 9/253* (2020.01); *G16H 10/20* (2018.01); *G16H 50/30* (2018.01)

(58) Field of Classification Search
CPC .......... G06K 19/06037; G06V 40/166; G06V 40/172; G06V 10/143; G06V 40/16; G07C 9/253; G07C 9/27; G07C 9/28; G16H 10/20; G16H 50/30; G16H 30/40; G16H 50/80
USPC .................. 705/1.1–912, 320, 325
See application file for complete search history.

(56) References Cited

U.S. PATENT DOCUMENTS

| | | | | |
|---|---|---|---|---|
| 2007/0222554 | A1* | 9/2007 | Hart | G07C 9/25 340/5.6 |
| 2015/0269331 | A1* | 9/2015 | Bolanos | G06F 21/34 705/51 |
| 2017/0032092 | A1* | 2/2017 | Mink | G06Q 10/1095 |
| 2018/0158555 | A1* | 6/2018 | Cashman | G06Q 10/1095 |
| 2019/0050550 | A1* | 2/2019 | Berini | G06V 10/28 |
| 2019/0192010 | A1* | 6/2019 | Mane | A61B 5/165 |
| 2020/0175255 | A1* | 6/2020 | Küçükcayir | G06V 40/172 |
| 2020/0372743 | A1* | 11/2020 | Miller | G07C 9/257 |
| 2021/0304537 | A1* | 9/2021 | Reed | G06F 18/22 |
| 2021/0390812 | A1* | 12/2021 | Chaurasia | G07C 9/27 |
| 2021/0391089 | A1* | 12/2021 | Eswara | G16H 40/20 |
| 2022/0036678 | A1* | 2/2022 | Parekh | G07C 9/25 |
| 2022/0130534 | A1* | 4/2022 | Romanychev | G16H 40/67 |
| 2023/0112547 | A1* | 4/2023 | Satish | A61B 5/7275 705/2 |

OTHER PUBLICATIONS

Maras, E. (2020). Temperature check kiosks ready to tackle COVID-19. Food Truck Operator. News Features. Networld Media Group DBA Networld Alliance, LLC. (May 27, 2020). (Year: 2020).*

"EBI workplace health & safety solution provides the confidence employees need to return to the office safely and the insights and tools for organizations to manage safety workflows, policies, and operations cost-effectively during COVID-19." (Oct. 7, 2020). PR Newswire (Year: 2020).*

* cited by examiner

INTEGRATING HEALTHCARE SCREENING WITH OTHER IDENTITY-BASED FUNCTIONS

TECHNICAL FIELD

The present disclosure relates generally to healthcare screening, and, more particularly, to integrating healthcare screening with other identity-based functions.

BACKGROUND

Many facilities implement physical access control limiting who can enter, defining when entry is appropriate, and regulating how many people can be in a facility at a time. For example, a facility may desire to limit facility access to healthy people that are wearing face coverings. Another facility may desire to limit facility access to healthy employees that are wearing face coverings.

In addition to access control systems, facilities may have other systems keyed to employees, such as, human resource systems, payroll systems, etc. Access control systems and these other facility systems can be siloed from one another making interoperation between the systems difficult.

BRIEF DESCRIPTION OF THE DRAWINGS

The specific features, aspects and advantages of the present invention will become better understood with regard to the following description and accompanying drawings where.

DETAILED DESCRIPTION

The present invention extends to methods, systems, and computer program products for integrating healthcare screening with other identity-based functions.

In general, components facilitating healthcare screening interoperate with and/or are integrated into other systems, including facility access, identity, time keeping, payroll, etc. Aspects of the invention include using facial recognition to improve healthcare screening and satisfy governmental regulations (e.g., Center for Disease Control (CDC) guidelines). A thermal scanner can include a camera and an InfraRed (IR) camera. The thermal scanner can collect a facial image and derive a temperature for a person (e.g., from an IR image), such as, a person attempting to enter a facility. The thermal scanner can also collect or access previously collected healthcare screening questionnaire answers. The collected temperate and healthcare screening questionnaire answers can be used to control access to the facility. For example, the person can be denied access to the facility when the collected temperature exceeds a defined temperate threshold and/or healthcare screening questionnaire answers indicate the person may be sick.

The facial image, derived temperature data, and healthcare screening questionnaire answers can be combined into a database record corresponding to the person. The database record can be uploaded to a cloud server. Facilities may also need to identify and distinguish between employees and visitors, generate daily/weekly reports, get alerts, and using time clocking (i.e., clocking employees in and out). Facilities can utilize the database records stored at a cloud server to perform these and other functions.

For example, a facility can use a database record in combination with employee badge data to verify employee identity. A card reader can scan an employee badge to obtain badge data. The thermal scanner can use badge data to access a previously stored image of an employee. The thermal scanner can compare the previously stored image to collected image. A facial recognition algorithm can be utilized to determine a probability of a person in the previously stored image and the person in the collected image being the same person. If the probability is below a threshold (i.e., is the person is unlikely to be the employee), facility access can be denied. If the probability is equal to or above a threshold (i.e., is the person is likely to be the employee), facility access can be allowed and the employee clocked-in for work.

Alternately, a captured image can be sent to an employee cloud server. The employee cloud server can perform image comparisons and return results, such as, a probability of a person present an access card being the employee corresponding to the access card, whether facility access is allowed or denied, etc.

More generally, the thermal scanner may compare a collected image to images in an employee database to determine if a person is an employee or a visitor. Retention policies for database records corresponding to visitors can different from retention polices corresponding to employees. Alternately, a captured image can be sent to an employee cloud server. The employee cloud server can perform image comparisons and return results, such as, is a person a facility employee or non-employee, whether facility access is allowed or denied, etc.

In one aspect, a mask detection algorithm is utilized to determine if a person is wearing a face covering. The mask detection algorithm can be implemented at the thermal scanner or at an appropriate cloud server.

Healthcare screening questionnaire answers can be collected in different ways. In one aspect, the thermal scanner includes a touch screen display. The thermal scanner can present healthcare screening questions at the touch screen display. The person can enter answers to the healthcare screening questions at the touch screen display.

In another aspect, a person uses a mobile device to request a healthcare screening questionnaire from cloud-based storage. The person supplies answers to the healthcare screening questions at the mobile device. The cloud-based storage stores the answers in association with a link. The link is coded into a QR code and sent to the mobile device. The thermal scanner can use the camera to scan the QR code from the mobile device display. At the thermal scanner, a QR decoder can decode the link from the QR code. The thermal scanner can use the link to access the answers from the cloud-based storage.

In the vicinity of the thermal scanner, other hardware components can be activated in response to a person being allowed or denied access to a facility. When a person is allowed facility access, an access control component (e.g., a gate) can allow the person to pass and a printer can print a message indicating that the person is to proceed forward. When a person is denied facility access, the access control component (e.g., the gate) can prevent the person from passing pass and the printer can print a message. The printed message can indicate why access is denied (temperature to high, failed healthcare screening questionnaire, not an employee, not the employee corresponding to a badge, etc.) and/or provide further instructions, such as, "please see a doctor", "go to security", etc.

Figure 1:
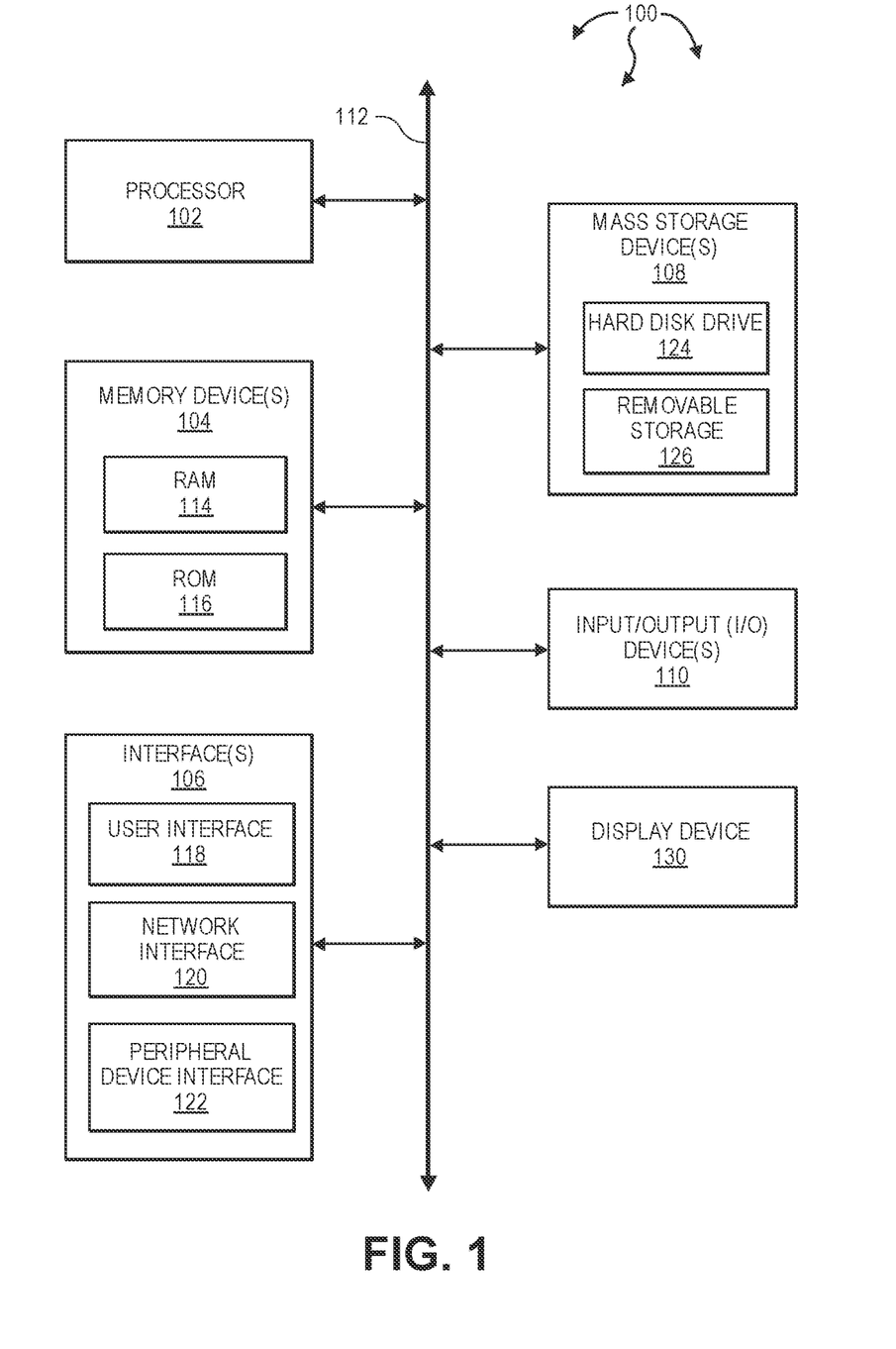
FIG. 1 illustrates an example block diagram of a computing device.

FIG. 1 illustrates an example block diagram of a computing device 100. Computing device 100 can be used to perform various procedures, such as those discussed herein. Computing device 100 can function as a server, a client, or any other computing entity. Computing device 100 can perform various communication and data transfer functions as described herein and can execute one or more application programs, such as the application programs described herein. Computing device 100 can be any of a wide variety of computing devices, such as a mobile telephone or other mobile device, a desktop computer, a notebook computer, a server computer, a handheld computer, tablet computer and the like.

Computing device 100 includes one or more processor(s) 102, one or more memory device(s) 104, one or more interface(s) 106, one or more mass storage device(s) 108, one or more Input/Output (I/O) device(s) 110, and a display device 130 all of which are coupled to a bus 112. Processor(s) 102 include one or more processors or controllers that execute instructions stored in memory device(s) 104 and/or mass storage device(s) 108. Processor(s) 102 may also include various types of computer storage media, such as cache memory. Processor(s) 102 can be real or virtual and can be allocated from on-premise, cloud computing, or any cloud provider resources.

Memory device(s) 104 include various computer storage media, such as volatile memory (e.g., random access memory (RAM) 114) and/or nonvolatile memory (e.g., read-only memory (ROM) 116). Memory device(s) 104 may also include rewritable ROM, such as Flash memory. Memory device(s) 104 can be real or virtual and can be allocated from on-premise, cloud computing, or any cloud provider resources.

Mass storage device(s) 108 include various computer storage media, such as magnetic tapes, magnetic disks, optical disks, solid state memory/drives (e.g., Flash memory), and so forth. As depicted in FIG. 1, a particular mass storage device is a hard disk drive 124. Various drives may also be included in mass storage device(s) 108 to enable reading from and/or writing to the various computer readable media. Mass storage device(s) 108 include removable media 126 and/or non-removable media. Mass storage device(s) 108 can be real or virtual and can be allocated from on-premise, cloud computing, or any cloud provider resources.

I/O device(s) 110 include various devices that allow data and/or other information to be input to or retrieved from computing device 100. Example I/O device(s) 110 include cursor control devices, keyboards, keypads, barcode scanners, microphones, monitors or other display devices, speakers, printers, network interface cards, modems, cameras, lenses, radars, CCDs or other image capture devices, and the like. I/O device(s) 110 can be real or virtual and can be allocated from on-premise, cloud computing, or any cloud provider resources.

Display device 130 includes any type of device capable of displaying information to one or more users of computing device 100. Examples of display device 130 include a monitor, display terminal, video projection device, and the like. Display device 130 can be real or virtual and can be allocated from on-premise, cloud computing, or any cloud provider resources.

Interface(s) 106 include various interfaces that allow computing device 100 to interact with other systems, devices, or computing environments as well as humans. Example interface(s) 106 can include any number of different network interfaces 120, such as interfaces to personal area networks (PANs), local area networks (LANs), wide area networks (WANs), wireless networks (e.g., near field communication (NFC), Bluetooth, Wi-Fi, etc., networks), and the Internet. Other interfaces include user interface 118 and peripheral device interface 122. Interface(s) 106 can be real or virtual and can be allocated from on-premise, cloud computing, or any cloud provider resources.

Bus 112 allows processor(s) 102, memory device(s) 104, interface(s) 106, mass storage device(s) 108, and I/O device(s) 110 to communicate with one another, as well as other devices or components coupled to bus 112. Bus 112 represents one or more of several types of bus structures, such as a system bus, PCI bus, IEEE 1394 bus, USB bus, and so forth. Bus 112 can be real or virtual and can be allocated from on-premise, cloud computing, or any cloud provider resources.

Figure 2A:
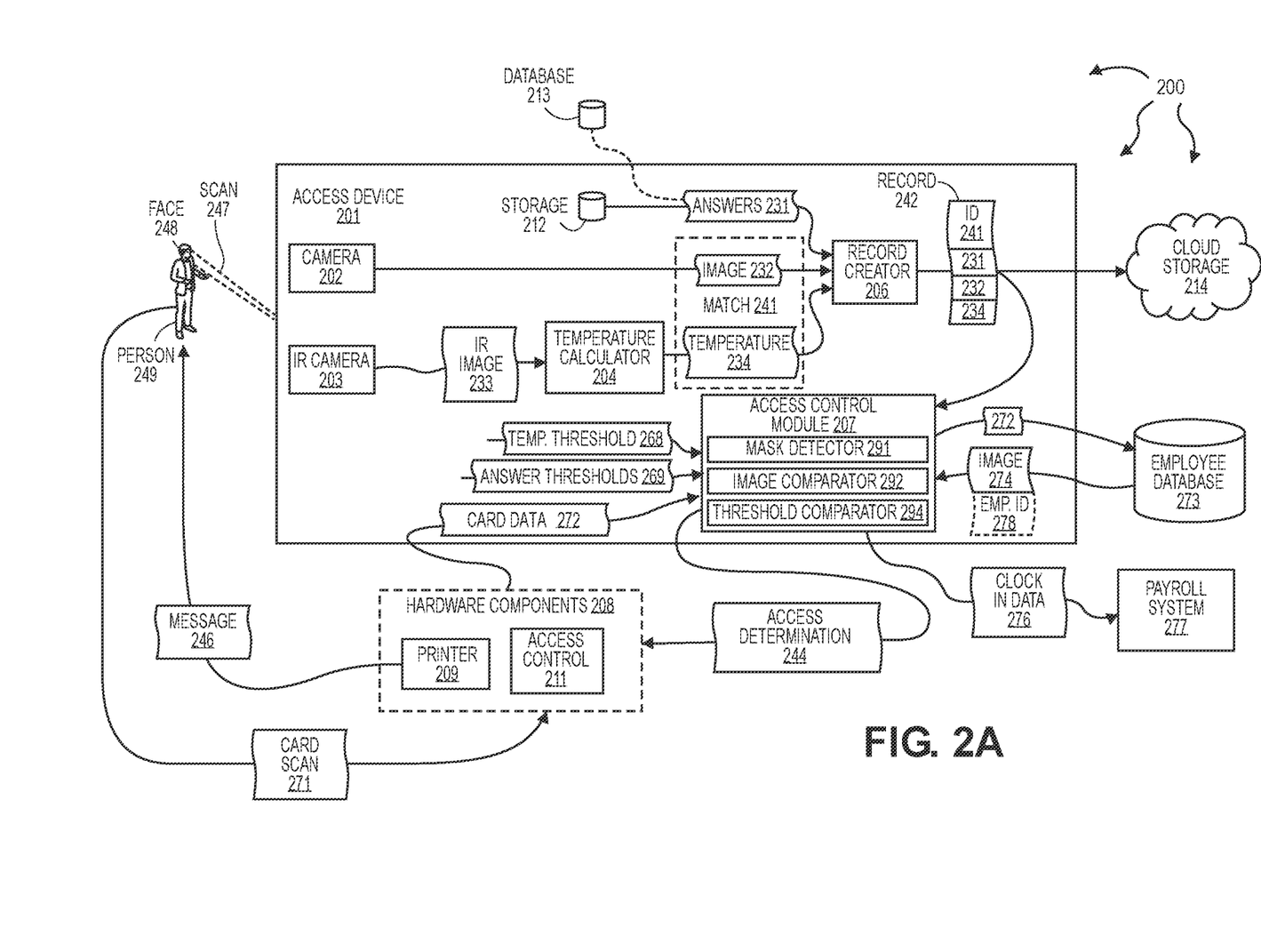
FIG. 2A illustrates an example computer architecture that facilitates integrating healthcare screening with other identity-based functions at a facility.

FIG. 2A illustrates an example computer architecture 200 that facilitates integrating healthcare screening with other identity-based functions. As depicted, computer architecture 200 includes access device 201, hardware components 208, database 213, cloud storage 214, employee database 273, and payroll system 277. Access device 201, hardware components 208, database 213, cloud storage 214, employee database 273, and payroll system 277 can be connected to (or be part of) a network, such as, for example, a Local Area Network ("LAN"), a Wide Area Network ("WAN"), and even the Internet. Accordingly, access device 201, hardware components 208, database 213, cloud storage 214, employee database 273, and payroll system 277 as well as any other connected computer systems and their components can create and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), Simple Object Access Protocol (SOAP), etc. or using other non-datagram protocols) over the network.

In one aspect, access device 201 is physically located at an entrance to a facility (e.g., a store, an office building, etc.).

Access device 201 further includes camera 202, InfraRed (IR) camera 203, temperature calculator 204, record creator 206, access control module 207, and storage 212. Camera 202 can be configured to capture images (in the visual light spectrum) of faces. IR camera 203 can be configured to capture IR images of faces. Temperature calculator 204 is configured to calculate a human body temperature from an IR image of a face. Storage 212 can store locally collected healthcare screening questionnaire answers.

Database 213 is configured to store healthcare screening questionnaires and healthcare screening questionnaires answers. Healthcare screening questionnaires answers can be collected through other mobile devices, for example, mobile phones.

Access device 201 can scan a person's face with camera 202 and IR camera 203, essentially simultaneously capturing an image and an (IR) image of the person's face. Temperature calculator 204 calculate a human body temperature from the IR image of the person's face. Access device 201 can match the captured image to the calculated temperature.

Record creator 206 is configured to access a matched captured image and calculated temperature for a person and healthcare screening questionnaire answers for the person (either from storage 212 or database 213). Record creator 206 can form a database record including the captured image, the calculated temperature, and the healthcare screening questionnaire answers. Record creator 206 can also assign a record identifier to the record. Record creator 206 can store the record in cloud storage 214. The record can be utilized for subsequent report generation.

As depicted, hardware components 208 include printer 209 and access control components 211. Access control components 211 can include access gates, card readers, etc.

Access control module 207 can also utilize the contents of database records for controlling facility access. As depicted, access control module 207 further includes mask detector 291, image comparator 292, and threshold comparator 294. Mask detector 291 is configured to analyze a captured image and determine a probability of the person in the image wearing a face covering. Image comparator 292 is configured to compare images and determine a probability that the images are of the same person. Threshold comparator 294 is configured to compare calculated temperatures to temperature thresholds and/or to compare healthcare screening questionnaire answers to answer thresholds. Access control module 207 can allow or deny facility access based on determinations of any of includes mask detector 291, image comparator 292, and threshold comparator 294.

In alternative aspects, one or more of mask detector 291, image comparator 292, and threshold comparator 294 are implemented at corresponding cloud servers.

In one aspect, access control module 207 denies facility access to a person when mask detector 291 determines a reduced probability of the person in a captured image wearing a face covering. A face covering threshold can be used. When a probability of a person wearing a mask is below the face covering threshold, facility access can be denied.

In another aspect, access control module 207 denies facility access to a person when image comparator 292 determines a reduced probability of a person being an employee. Access control module 207 can access previously stored employee images from employee database 273. Image comparator 292 can compare a captured image to previously stored employee images. If image comparator 292 identifies a sufficient match between a captured image and a previously stored employee image, access control module 207 determines the person in the captured image is an employee. When an employee is identified, access control components 211 can permit the person access to the facility and may also send appropriate clock in data to payroll system 277.

If image comparator 292 does not identify a sufficient match between a captured image and any previously stored employee image, access control module 207 determines the person in the captured image is not an employee. Instead, the person may be a non-employee or a visitor Access control module 207 may deny facility access to and/or implement different access processing for a visitor or other non-employee.

Along with facial scanning to capture an image and an IR image, a person may present an access card (e.g., a proximity card) at a card reader included in access control components 211. The card reader can read card data from the access card and send the card data to access control module 207. Access control module 207 can use the card data to access a corresponding employee record, including a previously stored employee image, from employee database 273. Image comparator 292 can compare a captured image to the previously stored employee image.

In one aspect, access control module 207 allows facility access to a person when image comparator 292 determines an increased probability of a person presenting an employee access card actually being the employee corresponding to the employee access card. If image comparator 292 identifies a sufficient match between the captured image and the previously stored employee image, access control module 207 determines the person in the captured image is the employee associated with the access card. When the employee is identified, access control components 211 can permit the person access to the facility and may also send appropriate clock in data to payroll system 277.

In another aspect, access control module 207 denies facility access to a person when image comparator 292 determines a reduced probability of a person presenting an employee access card actually being the employee corresponding to the employee access card. If image comparator 292 does not identify a sufficient match between the captured image and the previously stored employee image, access control module 207 determines the person in the captured image is not the employee associated with the access card. Instead the person may be another employee, a non-employee, or a visitor. Access control module 207 may deny facility access to and/or implement different access processing when a person inappropriately uses an access card.

Accordingly, any of a number of factors can be considered when determining facility access, including, but not limited to, human body temperature, healthcare screening questionnaire answers, face covering status, employment status, access card presentation validity, etc. Access device 201 can also interoperate with and/or be integrated into any number of systems including cloud storage 214, employee database 273, payroll system 277, etc.

Figure 3:
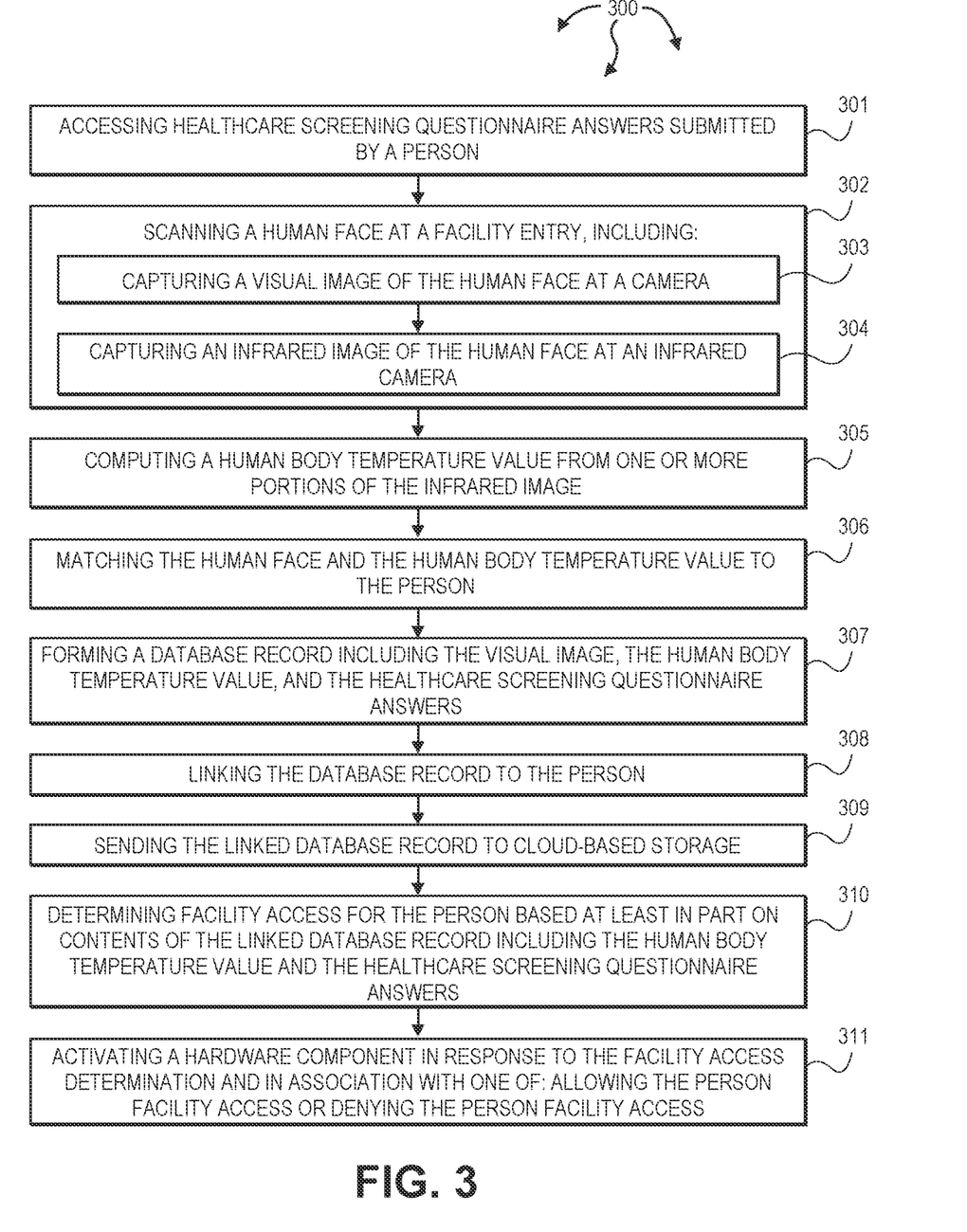
FIG. 3 illustrates a flow chart of an example method for integrating healthcare screening with facility access control.

FIG. 3 illustrates a flow chart of an example method for integrating healthcare screening with facility access control. Method 300 will be described with respect to the components and data in computer architecture 200.

Method 300 includes accessing healthcare screening questionnaire answers submitted by a person (301). For example, record creator 206 can access answers 231 submitted by person 249 from storage 212 or database 213.

Figure 2B:
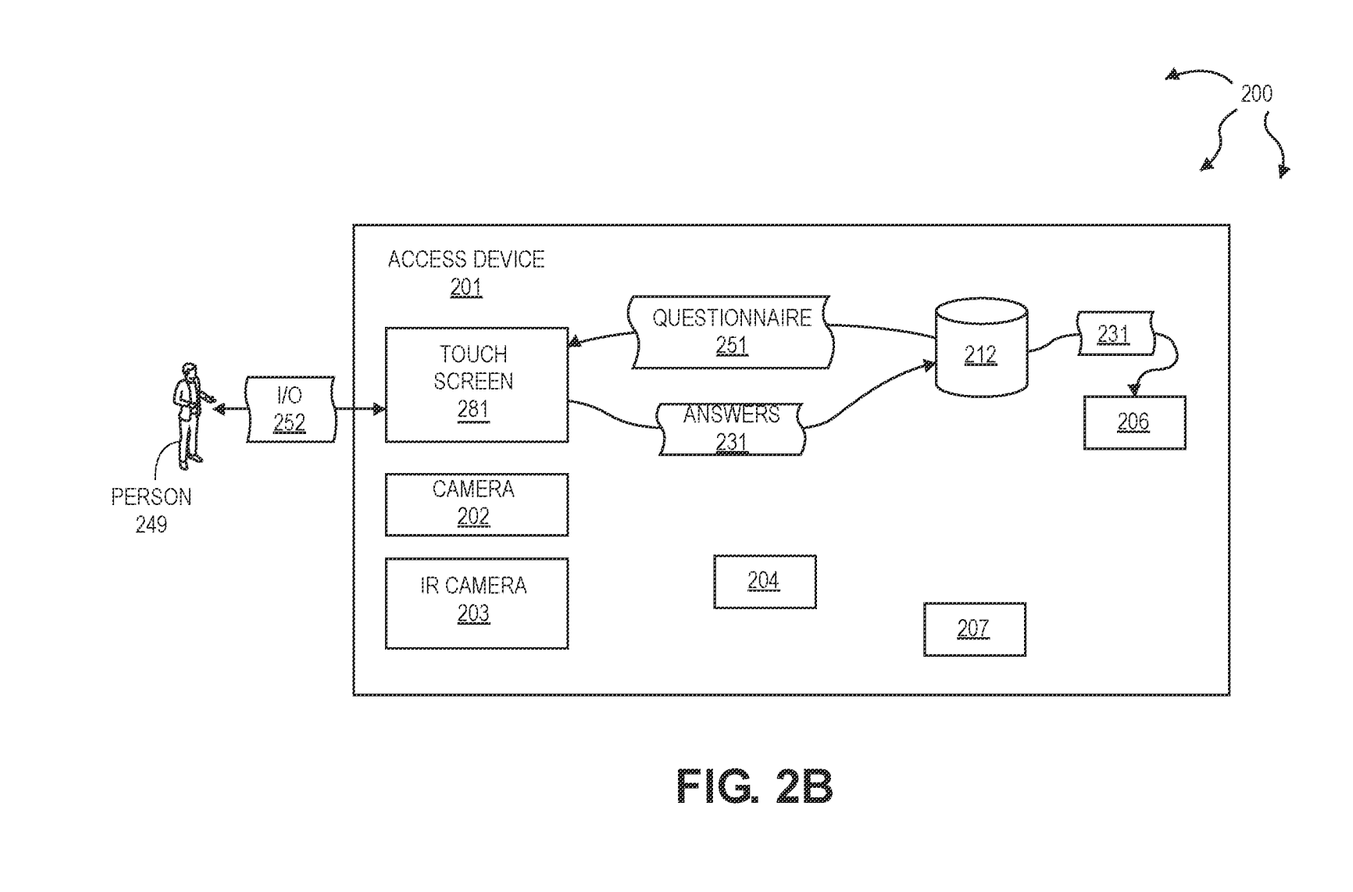
FIG. 2B illustrates an example computer architecture option that facilitates locally gathering healthcare screening questionnaire answers.

FIG. 2B illustrates an option of example computer architecture 200 that facilitates locally gathering healthcare screening questionnaire answers. Healthcare screening questionnaire 251 can be stored at storage 212. Access device 201 can present healthcare screening questionnaire 251 (e.g., as a sequence of questions) at touch screen 281. Person 249 can enter answers 231 to healthcare screening questionnaire 251 at touch screen 281. Input/output 252 collectively represents presenting healthcare screening questionnaire 251 and entering answers 231. Answers 231 can be stored at storage 212 and subsequently provided to record creator 206.

Figure 2C:
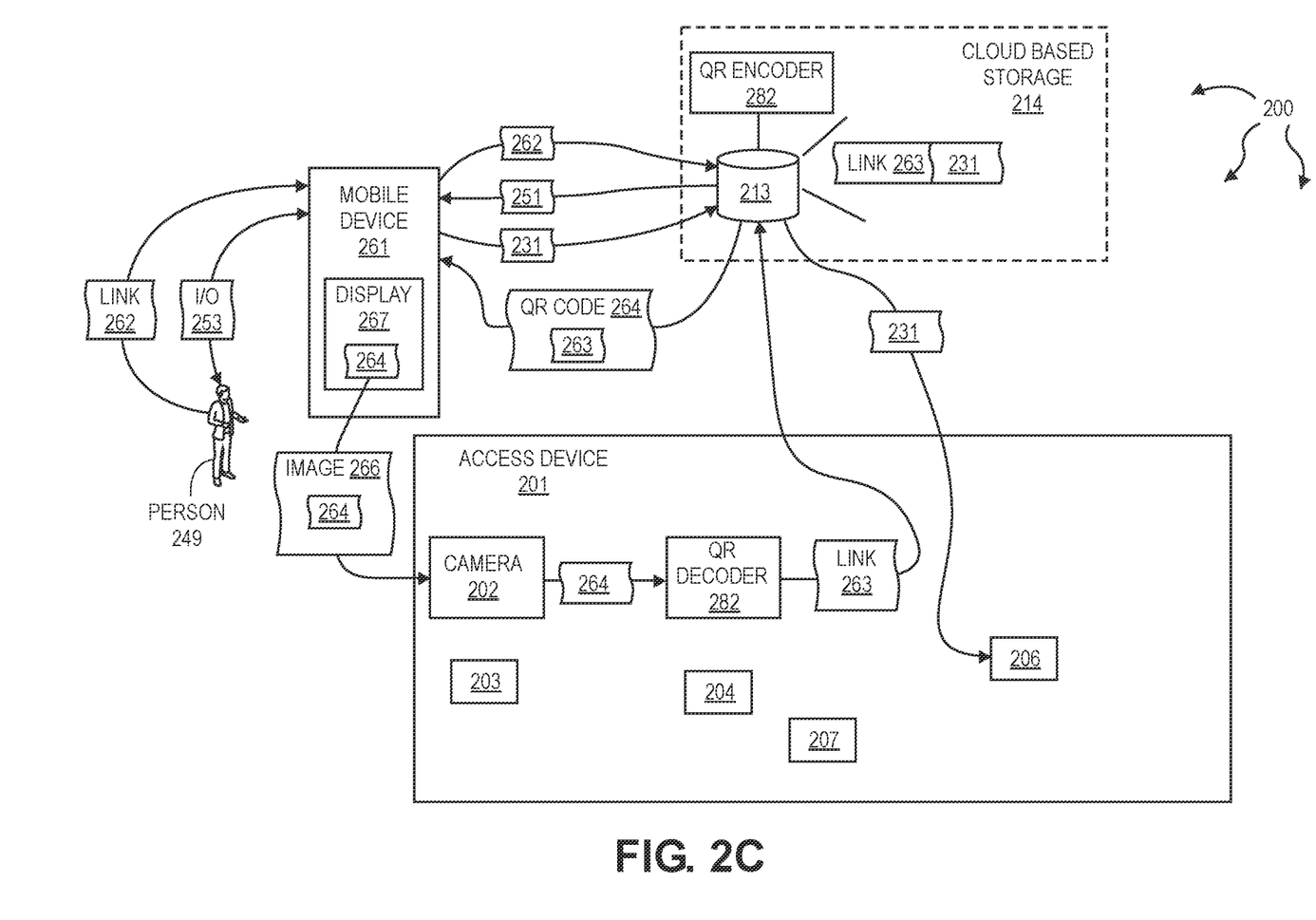
FIG. 2C illustrates another example computer architecture option that facilitates gathering healthcare screening questionnaire answers.

FIG. 2C illustrates another option of computer architecture 200 that facilitates gathering healthcare screening questionnaire answers. Person 249 can enter link 262 at mobile device 261. Mobile device 261 can use link 262 to access healthcare screening questionnaire 251 from database 213. Mobile device 261 can present healthcare screening questionnaire 251 (e.g., as a sequence of questions) at display 267. Person 249 can enter answers 231 to healthcare screening questionnaire 251 at display 267. Input/output 253 collectively represents presenting healthcare screening questionnaire 251 and entering answers 231.

Cloud based storage 214 can associate link 263 with answers 231. Link 263 can be stored along with answers 231 in database 213. QR encoder 282 can encode link 263 into QR code 264. Could based storage 214 can send QR code 264 to mobile device 261. Mobile device 261 can display QR code 264 at display 267. Camera 202 can capture image 266 (of display 267) including QR code 264. QR decoder 282 can decode link 263 from QR code 264. Access device 201 can submit link 263 to database 213. In response, database 213 can return answers 231 to access device 201. Answers 231 can be accessed by record creator 206. Accordingly, healthcare screen questionnaire answers can be provided without touching access device 201.

Method 300 includes scanning a human face at a facility entrance (302). For example, returning to FIG. 2A, access device 201 can scan 247 face 248 of person 249. Scanning a human face includes capturing a visual image of the human face at a camera (303). For example, camera 202 can capture image 232 of face 248. Scanning a human face includes capturing an infrared image of the human face at an infrared camera (304). For example, IR camera 203 can capture InfraRed (IR) image 233 of face 248. Method 300 includes computing a human body temperature value from one or more portions of the infrared image (305). For example, temperature calculator 204 can calculate temperature 234 from one or more portions of IR image 233.

Method 300 includes matching the human face and the human body temperature value to the person (306). For example, access device 241 can match 241 image 232 and temperature 234 to person 249. Method 300 includes forming a database record including the visual image, the human body temperature value, and the healthcare screening questionnaire answers (307) and linking the database record to the person (308). For example, record creator 206 can create record 242 including image 231, temperature 234, and answers 231. Record creator 206 can associate identifier 241 with person 249 and include identifier 241 in record 242. Method 300 includes sending the linked database record to cloud-based storage (309). For example, access device 201 can send record 242 to cloud storage 214. Record 242 can be used for subsequent daily or weekly reports.

Method 300 includes determining facility access for the person based at least in part on contents of the linked database record including the human body temperature value and the healthcare screening questionnaire answers (310). For example, access device 201 derive facility access determination 244 for person 249 based at least in part on temperature 234 and answers 231. Access determination 244 can indicate allowed facility access or denied facility access for person 249.

Threshold comparator 294 can compare temperature 234 to temperature threshold 268 and can compare answers 231 to answer thresholds 269. Mask detector 291 can also determine a probability that person 249 is wearing a face covering from image 232.

If the probability of person 249 wearing a face covering is insufficient, access determination 244 can deny person 249 facility access. If temperature 234 exceeds temperature threshold 260 (e.g., over 100 degrees), access determination 244 can deny person 249 facility access. If answers 231 fail to satisfy answer thresholds 269, access determination 244 can deny person 249 facility access.

When the probability of person 249 wearing a mask sufficient, temperature 234 is at or below temperature threshold 260, and answers 231 satisfy answer thresholds 269, access determination 244 can allow person 249 facility access.

In one aspect, access control module 207 accesses employee images from employee database 273. Access control module can access employee images for any employees that work at the facility. Image comparator 292 compares image 232 to any accessed employee images and determines if image 232 sufficiently matches an employee image. When image 232 sufficiently matches an employee image, access control module 207 detects that person 249 is a facility employee. Access control module 207 can allow facility access to employees. As such, access determination 244 can allow person 249 facility access.

When an employee is detected, access control module 207 can also send appropriate clock in data 276 for the employee to payroll system 277.

On the other hand, when image 232 does not sufficiently match any employee image, access control module 207 detects that person 249 is not a facility employee. Access control module 207 can deny facility access to non-employees or refer non-employees for further processing. For example, access determination 244 can deny person 249 facility access.

In a further aspect, and concurrently with scan 247, person 249 presents a (e.g., proximity) card at a card reader included in access control hardware 211. The card reader scans 271 the card and accesses card data 272 from the card. The card reader sends card data 272 to access control module 207. Access control module 207 uses card data 272 to access employee image 274 (and potentially other employee information, such as, employee identifier 278) for the employee corresponding to card data 272.

Image comparator 292 compares image 232 to image 274 and determines if image 232 sufficiently matches an image 274. When image 232 sufficiently matches image 274, access control module 207 detects that person 249 is the employee depicted in image 274. Access control module 207 can allow facility access to a person presenting a card when a captured image of the person sufficiently matches a previously stored image of the employee corresponding to the card. As such, access determination 244 can allow person 249 facility access.

When person 249 is detected as the employee corresponding to card data 272, appropriate clock in data 276 can be sent to payroll system 277 to clock in the employee.

On the other hand, when image 232 does not sufficiently match image 274, access control module detects that person 249 is not the employee depicted in image 274. For example, person 249 can be a different employee, a non-employee, a visitor, etc. Access control module 207 can deny facility access to a person presenting a card when a captured image of the person does not sufficiently match a previously stored image of the employee corresponding to the card. For example, access determination 244 can deny person 249 facility access. Access control module 207 may also alert facility security of improper card usage.

Method 300 incudes activating a hardware component in response to the facility access determination and in association with one of: allowing the person facility access or denying the person facility access (311). For example, access control module 207 can send access determination 244 to hardware components 208. When access determination 244 denies person 249 facility access, printer 209 can be activated to print message 246 in the vicinity of person 249. Message 246 can indicate a reason for denial and/or may provide further instructions. When a temperature check has fair or healthcare screening answers fail, message 246 can instruct person 249 to "Please See A Doctor". When person 249 is not an employee or not an employee corresponding to scanned badge data, message 246 can instruct person 249 to "Please See Security". Access control components 211, for example, an access gate, can be activated to remain locked and prevent further access by person 249.

When access determination 244 allows person 249 facility access, printer 209 can be activated to print message 246 in the vicinity of person 249. Message 246 can instruct person 249 to "proceed forward" or can welcome person 249 to the facility. Access control components 211, for example, an access gate, can be activated to open and allow further access by person 249.

In some aspects, various functionality of access device 201 is alternately implemented at one or more cloud servers. For example, mask detection and/or image comparison can be implemented at corresponding cloud servers. Images can be sent from access device 201 to cloud servers. The cloud servers can implement mask detection and/or image comparison and return results back to access device 201.

Figure 4:
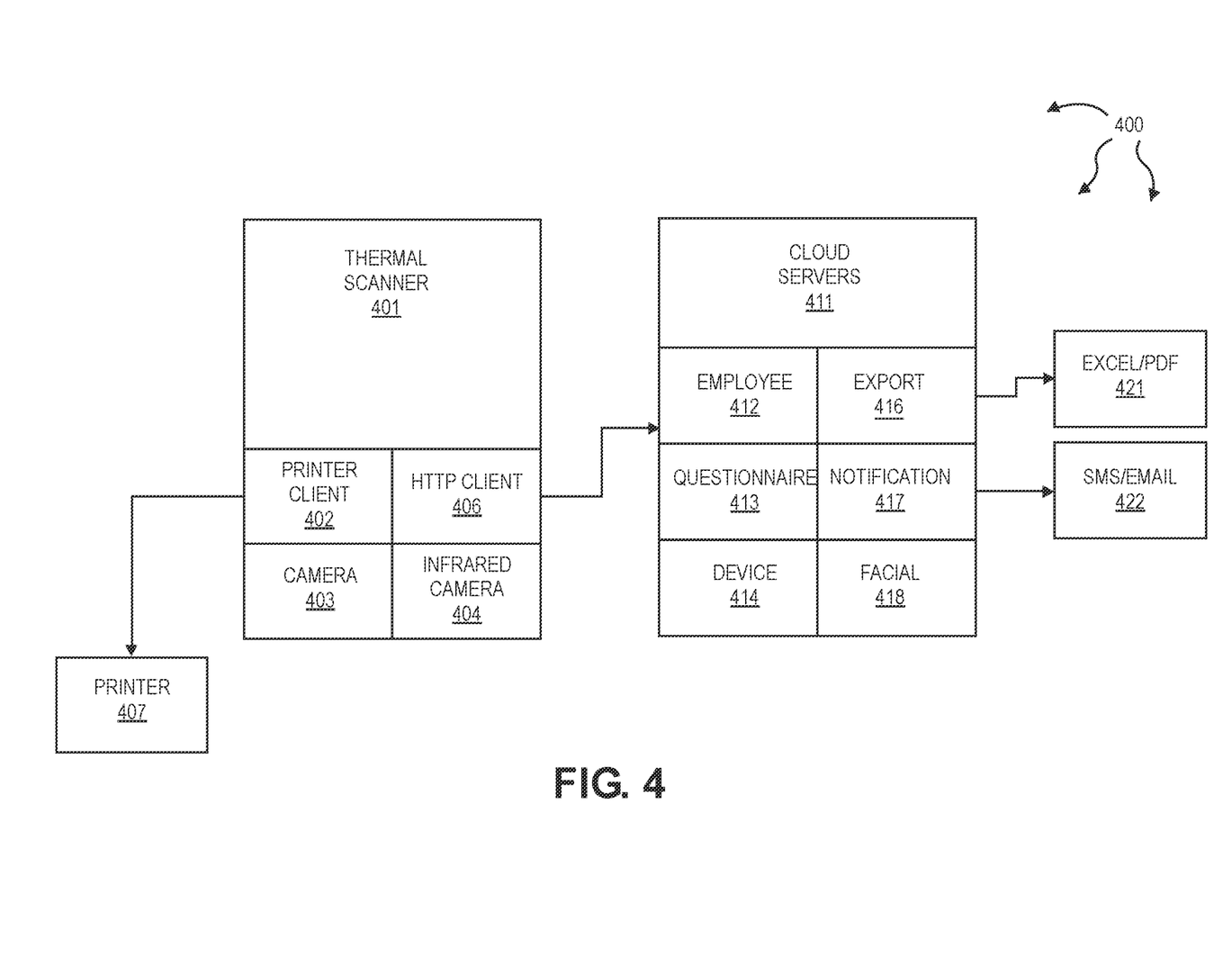
FIG. 4 illustrates an example computer architecture of an integrated healthcare screening system.

FIG. 4 illustrates an example computer architecture 400 of an integrated healthcare screening system. As depicted, computer architecture 400 include thermal scanner 401, printer 407, and cloud servers 411. Thermal scanner 401 further includes a printer client 402, a camera, 403, an IR camera 404, and an HTTP client 406. Printer client 402 can be used to print messages at printer 407. HTTP client 406 can be used to exchange data with cloud servers 411.

Cloud servers 411 includes employee 412, questionnaire 413, device 414, export 416, notification 417, and facial 418. Employee 412 can be a cloud server storing and managing employee data (e.g., similar to employee database 273). Questionnaire 413 can similar to storage 212 and/or database 213. Device 414 can manage device related functions, for example to collect the online/offline status of the scanner, to set parameters (temperature unit/limit, time zone etc.), etc.

Export 416 can export data related to facility access to various spreadsheet or graphical formats, such as, excel/PDF 421. Notification 417 can send notifications related to facility access via various electronic communication mediums, such as, SMS/Email 422. Facial 418 can be configured to perform facial recognition based on an image uploaded from scanner 401.

Figure 5:
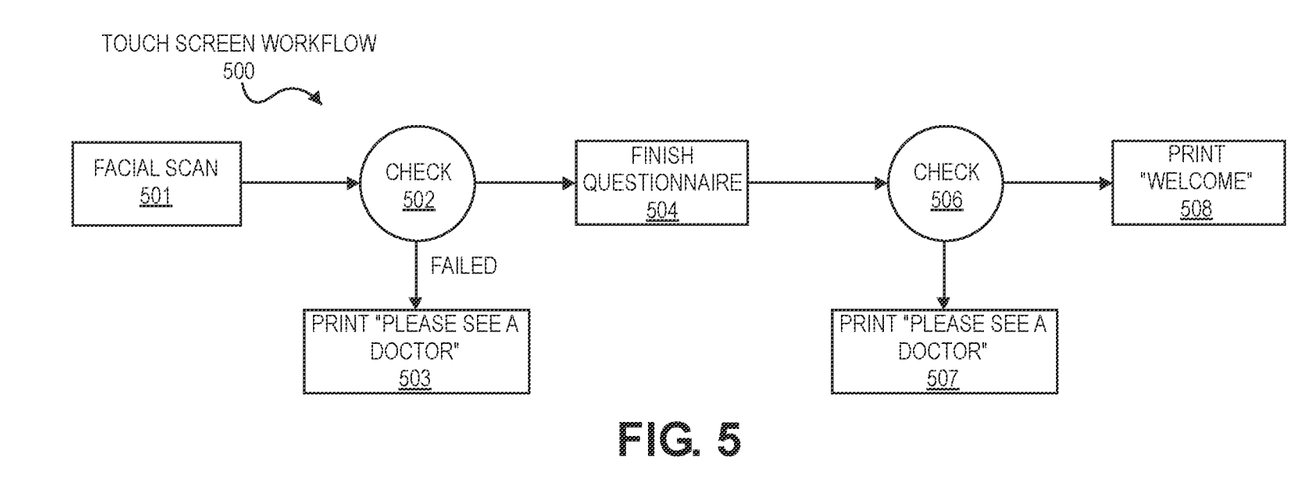
FIG. 5 illustrates a healthcare screening workflow.

FIG. 5 illustrates a healthcare screening workflow 500 (e.g., implemented using components in FIG. 2B). A thermal device (e.g., access control device 201) performs facial scan 501 of a person. From the facial scan (i.e., an IR image), the thermal device can check 502 the person's temperature. If the person's temperature exceeds a threshold value (failure), a "Please See a Doctor" message 503 is printed. On the other hand, if the person's temperature is at or below the threshold value, the person is allowed to finish a healthcare screening questionnaire 504 (e.g., on a touch screen of thermal device).

The thermal device checks 506 answers to healthcare screening questionnaire. If the answers to the healthcare screening questionnaire indicate greater than a threshold probability of the person being sick, a "Please See a Doctor" message 507 is printed. On the other hand, if the answers to the healthcare screening questionnaire indicate less than a threshold probability of the person being sick, a "Welcome" message 508 is printed.

Figure 6:
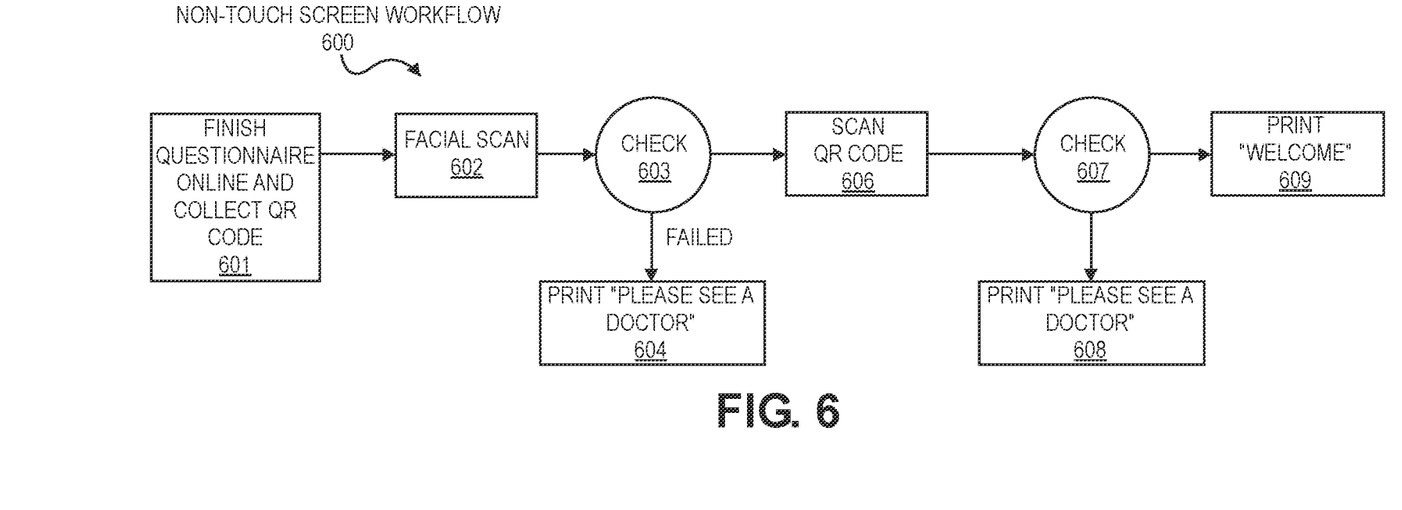
FIG. 6 illustrates another healthcare screening workflow.

FIG. 6 illustrates another healthcare screening workflow 600 (e.g., implemented using components in FIG. 2C). A person finishes a healthcare screening questionnaire online and collects a corresponding QR code 601. A thermal device (e.g., access control device 201) performs facial scan 602 of a person. From the facial scan (i.e., an IR image), the thermal device can check 603 the person's temperature. If the person's temperature exceeds a threshold value (failure), a "Please See a Doctor" message 603 is printed. On the other hand, if the person's temperature is at or below the threshold value, the thermal device scans the QR code 606.

The thermal device uses contents of the QR code (e.g., a decoded link) to access answers corresponding to the online healthcare screening questionnaire. The thermal device checks 607 answers to healthcare screening questionnaire. If the answers to the healthcare screening questionnaire indicate greater than a threshold probability of the person being sick, a "Please See a Doctor" message 608 is printed. On the other hand, if the answers to the healthcare screening questionnaire indicate less than a threshold probability of the person being sick, a "Welcome" message 609 is printed. Accordingly, a healthcare screening can be implemented without touching a thermal device.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations can comprise or utilize a special purpose or general-purpose computer including computer hardware, such as, for example, one or more computer and/or hardware processors (including any of Central Processing Units (CPUs), and/or Graphical Processing Units (GPUs), general-purpose GPUs (GPGPUs), Field Programmable Gate Arrays (FPGAs), application specific integrated circuits (ASICs), Tensor Processing Units (TPUs)) and system memory, as discussed in greater detail below. Implementations also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations can comprise at least two distinctly different kinds of computer-readable media: computer storage media (devices) and transmission media.

Computer storage media (devices) includes RAM, ROM, EEPROM, CD-ROM, Solid State Drives (SSDs) (e.g., RAM-based or Flash-based), Shingled Magnetic Recording (SMR) devices, storage class memory (SCM), Flash memory, phase-change memory (PCM), other types of memory, other optical disk storage, magnetic disk storage or other magnetic storage devices, or any other medium which can be used to store desired program code means in the form of computer-executable instructions or data structures and which can be accessed by a general purpose or special purpose computer.

In one aspect, one or more processors are configured to execute instructions (e.g., computer-readable instructions, computer-executable instructions, etc.) to perform any of a plurality of described operations. The one or more processors can access information from system memory and/or store information in system memory. The one or more processors can (e.g., automatically) transform information between different formats, such as, for example, between any of: facial scans, images, InfraRed (IR) images, calculated temperatures, healthcare screening questionnaires, healthcare screening questionnaires answers, record identifiers, temperature thresholds, answer thresholds, card data, access determinations, clock in data, cloud storage records, printer messages, card scans, links, QR codes, person input/output, reports, exports, electronic messages, etc.

System memory can be coupled to the one or more processors and can store instructions (e.g., computer-readable instructions, computer-executable instructions, etc.) executed by the one or more processors. The system memory can also be configured to store any of a plurality of other types of data generated and/or transformed by the described components, such as, for example, facial scans, images, InfraRed (IR) images, calculated temperatures, healthcare screening questionnaires, healthcare screening questionnaires answers, record identifiers, temperature thresholds, answer thresholds, card data, access determinations, clock in data, cloud storage records, printer messages, card scans, links, QR codes, person input/output, reports, exports, electronic messages, etc.

Implementations of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

The described aspects can also be implemented in cloud computing environments. In this description and the following claims, "cloud computing" is defined as a model for enabling on-demand network access to a shared pool of configurable computing resources. For example, cloud computing can be employed in the marketplace to offer ubiquitous and convenient on-demand access to the shared pool of configurable computing resources (e.g., compute resources, networking resources, and storage resources). The shared pool of configurable computing resources can be provisioned via virtualization and released with low effort or service provider interaction, and then scaled accordingly.

A cloud computing model can be composed of various characteristics such as, for example, on-demand self-service, broad network access, resource pooling, rapid elasticity, measured service, and so forth. A cloud computing model can also expose various service models, such as, for example, Software as a Service ("SaaS"), Platform as a Service ("PaaS"), and Infrastructure as a Service ("IaaS"). A cloud computing model can also be deployed using different deployment models such as on premise, private cloud, community cloud, public cloud, hybrid cloud, and so forth. In this description and in the following claims, a "cloud computing environment" is an environment in which cloud computing is employed.

Hybrid cloud deployment models combine portions of other different deployment models, such as, for example, a combination of on premise and public, a combination of private and public, a combination of two different public cloud deployment models, etc. Thus, resources utilized in a hybrid cloud can span different locations, including on premise, private clouds, (e.g., multiple different) public clouds, etc.

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

The invention claimed is:

1. A method comprising:
sending a healthcare screening questionnaire to a computing device of a person;
receiving healthcare screening questionnaire answers from the computing device;
storing the healthcare screening questionnaire answers in a cloud-based storage;
encoding a link to the healthcare screening questionnaire answers into a QR code;
sending the QR code to the computing device;
capturing an infrared image of a human face of the person using an infrared camera at a facility entry;
computing a human body temperature value from one or more portions of the infrared image;
in response to the human body temperature being greater than a threshold, displaying a message and denying access to the facility; and
in response to the human body temperature being at or below the threshold:
scanning, using a camera at the facility entry, the QR code displayed on the computing device by the person;
decoding the link from the QR code and submitting the link to the cloud-based storage;
receiving, from the cloud-based storage based on the link, the healthcare screening questionnaire answers submitted by the person;
determining facility access for the person based at least in part on the healthcare screening questionnaire answers; and
activating a hardware component in response to the facility access determination and in association with one of: allowing the person facility access or denying the person facility access.

2. The method of claim 1, further comprising:
capturing a visual image of the human face using the camera at the facility entry; and
matching the human face to a facility employee.

3. The method of claim 2, further comprising:
receiving employee badge data corresponding to a facility employee's employee badge from access control hardware controlling access to the facility;
accessing a previously captured visual image of the facility employee;
comparing the visual image to the previously captured visual image; and
validating the person as the facility employee based on the comparison.

4. The method of claim 3, further comprising:
forming a database record including the visual image, the human body temperature value, and the healthcare screening questionnaire answers; and
sending the database record to a facility time-keeping system clocking in the facility employee for work at the facility.

5. The method of claim 1, further comprising:
capturing a visual image of the human face using the camera at the facility entry; and
matching the human face to a facility visitor.

6. The method of claim 2, further comprising:
receiving employee badge data corresponding to a facility employee's employee badge from access control hardware controlling access to the facility;
accessing a previously captured visual image of the facility employee;
comparing the visual image to the previously captured visual image; and
determining that the person is not the employee based on the comparison.

7. The method of claim 6, wherein determining facility access for the person comprises denying the person facility access in view of the determination that the person is not the employee.

8. The method of claim 1, wherein determining facility access for the person comprises denying the person facility access; and
wherein activating a hardware component comprises printing a message at a printer in the vicinity of the facility entry, the message instructing the person to visit a doctor.

9. The method of claim 8, wherein determining facility access for the person based at least in part on the healthcare screening questionnaire answers comprises:
determining that the healthcare screening questionnaire answers indicate the person is potentially sick; and
denying the person facility access in view of the healthcare screening questionnaire answers indicating the person is potentially sick.

10. The method of claim 1,
wherein activating a hardware component comprises printing a message welcoming the person to the facility at a printer in the vicinity of the facility entry.

11. The method of claim 10, wherein allowing the person facility access comprises determining that the human body temperature value is less than or equal to the threshold and determining that the healthcare screening questionnaire answers indicate the person is healthy.

12. The method of claim 1, further comprising:
capturing a visual image of the human face using the camera at the facility entry;
determining from the visual image that the person is not wearing a facial covering; and
wherein determining facility access comprises denying the person facility access in view of the determination that the person is not wearing a facial covering.

13. A system comprising:
a processor; and
system memory coupled to the processor and storing instructions configured to cause the processor to:
send a healthcare screening questionnaire to a computing device of a person;
receive healthcare screening questionnaire answers from the computing device;
store the healthcare screening questionnaire answers in a cloud-based storage;
encode a link to the healthcare screening questionnaire answers into a QR code;
send the QR code to the computing device;
capture an infrared image of a human face of the person using an infrared camera at a facility entry;
compute a human body temperature value from one or more portions of the infrared image;
in response to the human body temperature being greater than a threshold, display a message and denying access to the facility; and
in response to the human body temperature being at or below the threshold:
scan, using a camera at the facility entry, the QR code displayed on the computing device by the person;
decode the link from the QR code and submitting the link to the cloud-based storage;
receive, from the cloud-based storage based on the link, the healthcare screening questionnaire answers submitted by the person;
determine facility access for the person based at least in part on the healthcare screening questionnaire answers; and
activate a hardware component in response to the facility access determination and in association with one of: allowing the person facility access or denying the person facility access.

14. The system of claim 13, wherein instructions configured to determine facility access for the person based at least in part on the healthcare screening questionnaire answers comprises instructions configured to:
determine that the healthcare screening questionnaire answers indicate the person is potentially sick; and
deny the person facility access in view of the healthcare screening questionnaire answers indicating the person is potentially sick.

* * * * *